US006576105B1

(12) United States Patent
Ma

(10) Patent No.: US 6,576,105 B1
(45) Date of Patent: Jun. 10, 2003

(54) PTERIDINE ANALYSIS BY CAPILLARY ELECTROPHORESIS USING LASER-INDUCED FLUORESCENCE DETECTION

(75) Inventor: Yinfa Ma, Kirksville, MO (US)

(73) Assignee: Truman State University, Kirksville, MO (US)

( * ) Notice: Subject to any disclaimer, the term of this patent is extended or adjusted under 35 U.S.C. 154(b) by 0 days.

(21) Appl. No.: 09/539,941

(22) Filed: Mar. 31, 2000

(51) Int. Cl.⁷ ............................................. G01N 27/447
(52) U.S. Cl. ..................................................... 204/451
(58) Field of Search ............................... 204/451, 456, 204/601, 606, 600, 450; 422/69; 210/656

(56) References Cited

PUBLICATIONS

Fuller et al. ("Single Neuron Analysis by Capillary Electrophoresis with Fluorescence Spectroscopy", Neuron, vol. 20, 173–181, Feb. 1998,.*

Han et al. ("Pteridine Analysis in Urine by Capillary Electrophoresis Using Laser Induced Fluorescence Detection", Anal. Chem. Apr., 1999, 71, 1265–1269).*

* cited by examiner

Primary Examiner—T. Tung
Assistant Examiner—Alex Noguerola
(74) Attorney, Agent, or Firm—McKee, Voorhees & Sease, P.L.C.

(57) ABSTRACT

The present invention provides a unique method and means for detecting pteridines in biological samples using the novel combination of capillary electrophoresis (CE) and laser-induced fluorescence detection (LIF). The method is effective in detecting eight pteridine compounds at very low detection limits of less than about $1 \times 10^{-10}$ M. The method allows for the detection of pteridines for various purposes involving metabolism and function investigation, including cancer monitoring and precancer screening.

16 Claims, 4 Drawing Sheets

PTERIDINE ANALYSIS BY CAPILLARY ELECTROPHORESIS USING LASER-INDUCED FLUORESCENCE DETECTION

BACKGROUND OF THE INVENTION

Pteridines are very important factors in human metabolism. Reduced pteridines are intermediates in anabolic and catabolic reactions and serve as coenzymes mediating the action of some enzymes. Pteridine and its derivatives play important roles in the synthesis of some vitamins, such as vitamin $B_2$ and vitamin $B_{10}$. Biopterin, neopterin, pterine, xanthopterin, and isoxanthopterin all belong to the pteridine family, which are well distributed in nature in living organisms.

Since pteridines are very important cofactors in the process of cell metabolism, their levels have significant importance in clinical diagnosis. They are excreted by humans in urine and the levels of pteridines have been found to elevate significantly when the cellular immune system is activated by certain diseases such as cancer, viral infections such as STDs and AIDS, and renal disease. Halpern, R. M. et al. *Proc. Natl. Acad. Sci. U.S.A.* 1977, 74, 587–591. Further investigation has shown that, for various tumors, quantitative alterations in the pteridine concentrations can be detected. Malignant tumors greatly disturb the biosynthesis and metabolism of pteridines, thus leading to a great change in pteridine concentrations. Each type of tumor shows its own pattern in changes of pteridine concentrations, since different pteridine derivatives may play various roles in different tumor-related disease. Goldberg, M. et al. *Pteridines* 1989, 1, 29–35.

Although the importance of various pteridines in cell metabolism of higher mammals was recognized decades ago, and some work had been carried out regarding the synthesis, reaction, and function of these compounds thereafter, the reason leading to the quantitative change of pteridines is still not fully understood. Kaufman, S. *Proc. Natl. Acad. Sci. U.S.A.* 1963, 50, 1085–1092. This is due primarily because the metabolism and regulation of pteridines have not been widely investigated due to the difficulties involved in quantitation.

High-performance liquid chromatography (HPLC) methods, such as cation-exchange chromatography, reversed-phase chromatography, and ion-pair chromatography have been employed as a tool for the quantitative measurement of pteridines. Woolf, J. H. et al. *J. Chromatogr.* 1983, 274, 398–402. However, these methods are time-consuming, not cost-effective, and have unsatisfactory separation. High-performance capillary electrophoresis (HPCE) is a very good alternative for HPLC due to its high efficiency, high speed, and small sample size requirements. HPCE coupled with UV spectrophotometric detection has been used as an alternative to separate different kinds of pteridines. Cha, K. W. et al. *Pteridines* 1993, 4, 210–213. However, this method is not suitable for practical purposes such as urine and serum analysis because the sensitivity of the UV detector is not high enough to detect the minute amount of pteridines in these kinds of clinical samples.

There is therefore a need in the art for a more accurate and sensitive method of detecting pteridines.

It is therefore a primary objective of the present invention to provide a method and means of detecting pteridines in clinical samples with sensitivity high enough to detect minute amounts of pteridines.

It is a further objective of the present invention to provide a method and means of detecting pteridines which is effective for use with clinical samples.

It is yet a further objective of the present invention to provide a method and means of detecting pteridines which is highly accurate.

It is still a further objective of the present invention to provide a method and means of detecting pteridines which has small sample size requirements.

It is a further objective of the present invention to provide a method and means of detecting pteridines which is fast and cost-effective.

These and other objectives will become apparent from the following detailed description of the invention.

SUMMARY OF THE INVENTION

The present invention sets forth a novel method and means for detecting pteridine levels in clinical samples. The method is based on high-performance capillary electrophoresis (CE) and laser-induced fluorescence (LIF) detection. CE provides better separation than high-performance liquid chromatography and the LIF detector enables the detection of minute amounts of pteridines in body fluid. The method is effective in detecting eight pteridine compounds at very low detection limits of less than $1\times10^{-10}$ M, and as low as $1\times10^{-11}$ M. At such detection limits, the method allows sufficient detection specificity and quantitation to diagnose elevated and decreased pteridine levels which are associated with cancer, and therefore may be used for purposes of cancer monitoring and for precancer screening.

DETAILED DESCRIPTION OF THE PREFERRED EMBODIMENT

Figure 1:
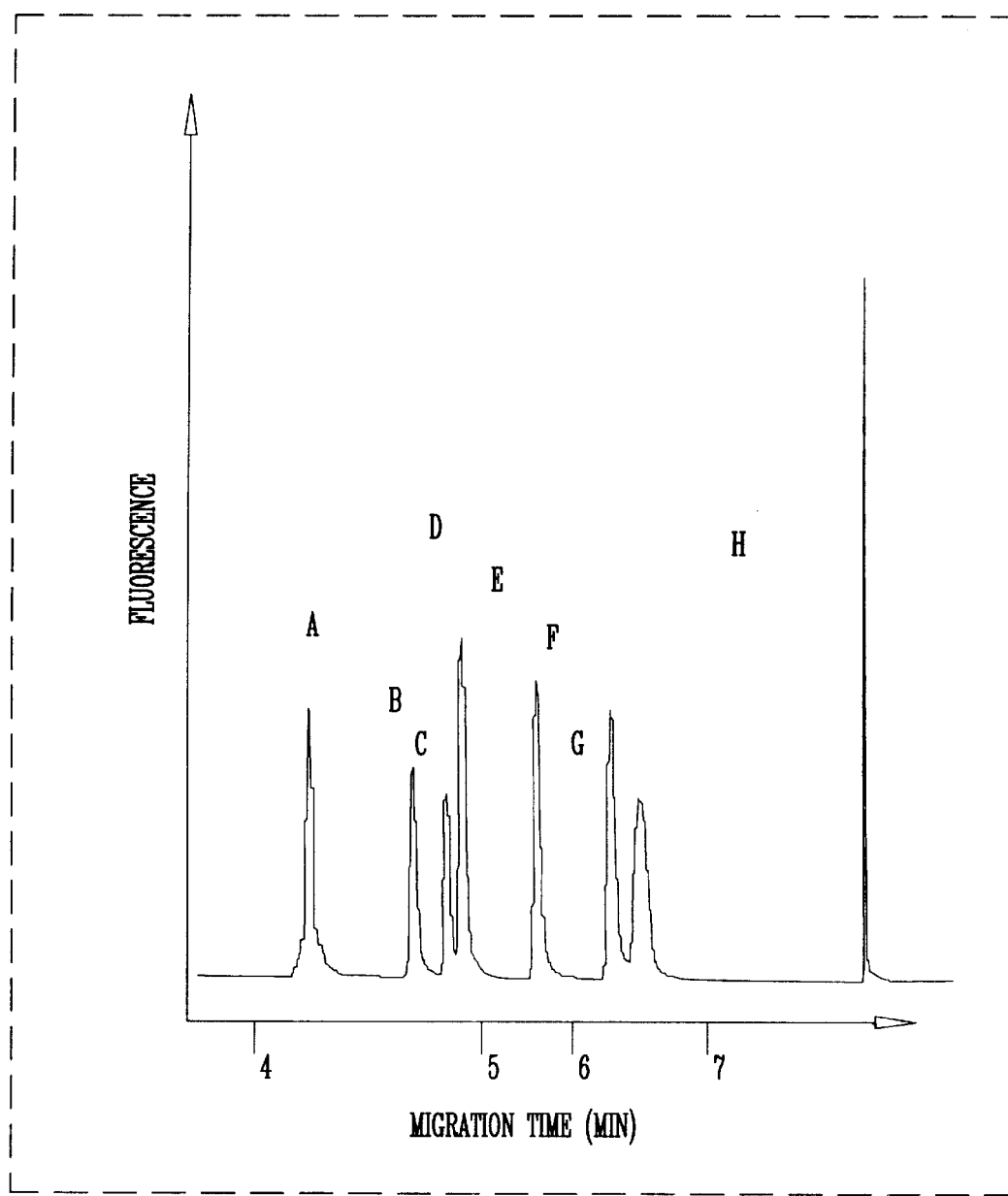
FIG. 1 is an electropherogram of the pteridine standards described in Example 1. Conditions: 0.1 M Tris-0.1 M borate-2 mM EDTA, pH 8.75; electrokinetic injection at 20 kV for 10 s; running at 20 kV; LIF detection at 325 nm/445 nm (ex/em). A, 6,7-dimethylpterin; B, 6-biopterin; C, D-(+)-neopterin; D, 6-(hydroxymethyl)pterine; E, pterine; F, isoxanthopterin; G, xanthopterin; H, pterin-6-carboxylic acid.

As set forth above, this invention describes for the first time the detection and quantitation of pteridine levels in clinical samples using a unique methodology of capillary electrophoresis (CE) coupled with laser-induced fluorescence (LIF) detection.

CE generally involves the application of high voltages across buffer-filled capillaries to achieve separations. Operation of a high-performance capillary electrophoresis (HPCE) system involves application of a high voltage (typically 10–30 kV) across a narrow bore (25–100 $\mu$m) capillary. The capillaries used are normally fused silica capillaries covered with an external polymer protective coating to give them increased mechanical strength. A small portion of this coating is removed to form a window for detection purposes. The window is aligned in the optical center of the detector. Capillaries are typically 25–100 cm long with 50 and 75 micron being the preferred inner diameter. On standard commercial high-performance capillary electrophoresis (HPCE) instruments, the capillary is typically held in a housing device as a cartridge to facilitate ease of capillary insertion into the instruction and to protect the delicate detection window area.

The capillary is filled with a buffer solution which conducts current through the inside of the capillary. The ends of the capillary are dipped into reservoirs filled with the buffer. Electrodes made of an inert material such as platinum are also inserted into the buffer reservoirs to complete the electrical circuit. Preferred operating buffers include tris (hydroxymethyl)aminomethane, 2-N-(morpholine) ethanesulfonic acid, N-(2-acetamido)iminodiacetic acid, piperazine-N,N'-bis(2-ethanesulfonic acid, N(2-acetamido)-2-aminoethanesulfonic acid, (2-aminoethyl)trimethyl-ammonium chloride hydrochloride, N,N-bis(2-hydroxy-ethyl)-2-aminoethane sulfonic acid, N-2-hydroxy-ethylpiperzine-N'-2-ethanesulfonic acid, N-tris (hydroxylmethyl)methylglycine, N-N-bis(2-hydroxyethyl)-glycine, 2-(N-cyclohexylamino)ethanesulfonic acid and mixtures thereof.

The present inventor has surprisingly found that the pH of the buffer solution is a critical factor in achieving sufficient separation of the pteridines from the sample. Specifically, the pH of the buffer used in accordance with this invention is preferably between about 8.4 to about 9.0, with about 8.6 to about 8.8 being most preferred.

It has further been found that the concentration of EDTA in the buffer influences the separation of pteridines while in a free condition. Specifically, the inventor has discovered that concentrations of up to about 2 mM EDTA enhances the separation of the two isomers, isoxanthopterin and xanthopterin. Quite unexpectedly, however, any increase in the concentration of EDTA beyond 2 mM inhibits the separation of pteridines. While it is not completely understood why this phenomena occurs, it is believed that EDTA may chelate ion impurities in the pteridine sample which in turn interferes with the separation of free pteridine.

Temperature has also been found to influence the separation of pteridines due to the change of mobility of the pteridines at various temperatures. The temperature of the pteridines during separation therefore should be in the range of from about 18° C. to 30° C., with from about 22° C. to 25° C. being preferred.

In the methods of this invention, a volume of clinical sample or other type of biochemical sample suspected of containing pteridines is introduced into one end of the capillary. The volume of sample is not critical and generally ranges from about 10–100 $\mu$l. The method of introduction of the sample is also not critical, and may be through any of the methods known in the art, including pressure injection and electrokinetic injection. A most preferred method of introduction is electrokinetic injection at 20 kV for about 10 seconds.

It has been found that for purposes of electrokinetic injection, the ionic strength of the sample matrix influences the detection limits of the pteridines. Specifically, the higher the ionic strength of the sample matrix, the lower the detection limit. For this reason, preferred sample matrixes include phosphate buffer, Tris-borate buffer, and Gly-Gly buffer.

It is preferred in the methods of this invention to oxidize the pteridines that may exist in reduced form in the sample such that the pteridines all exist in one form prior to introduction into the CE/LIF system for analysis. Any oxidizing agent that does not substantially interfere with the separation and detection of pteridines in the sample is appropriate for this purpose. A preferred oxidizing agent is iodine since it is easy to remove excess iodine from the sample prior to analysis. The pteridine samples are preferably processed in minimum light due to the light sensitivity of pteridines.

Irradiating pteridines in the 270–345 nm range generates fluorescence spectra. The excitation source for Laser Induced Fluorescence (LIF) in a preferred embodiment of the invention is a helium-cadmium laser operating in the range of about 320 to 330 nm, with about 325 nm being most preferred. The fluorescence produced by the sample is isolated and plotted with respect to time to form an electropherogram.

Using the methods of this invention, it has been found that pteridines can be well separated in as little as 10 minutes. The invention further enables detection of pteridine compounds at extremely low detection limits of less than $1 \times 10^{-10}$ M. The invention is therefore effective for use in clinical and biochemical laboratories for various purposes involving metabolism and function investigation, including cancer monitoring, precancer screening, clinical urinary analysis, and screening of pteridine concentration in blood donors. The methods of this invention are intended to be used with respect to all mammals, and especially with respect to higher mammals.

The following examples are offered to illustrate but not limit the invention. Thus, they are presented with the understanding that various formulation modifications as well as method of delivery modifications may be made and still be within the spirit of the invention.

EXAMPLE 1

EXPERIMENTAL SECTION

Chemicals and Reagents. Tris(hydroxymethyl) aminomethane (Tris) and the pteridine standards including 6-biopterin, pterin-6-carboxylic acid, pterine, D-(+)-neopterin, isoxanthopterin, xanthopterin, 6,7-dimethylpterine, and 6-(hydroxymethyl)pterin were all from Sigma (St. Louis, Mo.). Sodium hydroxide, dibasic sodium phosphate, EDTA disodium salt, and boric acid were purchased from Fisher (Fair Lawn, N.J.). Deionized water was prepared with a Milli-Q System (Millipore, Bedford, Mass.).

Buffer Preparation. The 0.1 M Tris-0.1 M borate-2 mM EDTA running buffer was prepared by dissolving 3.0285 g of Tris, 1.5453 g of boric acid, and 0.1861 g of EDTA-Na$_2$ into 150 mL of deionized water. After all the solids were dissolved, the pH of the buffer was adjusted to 8.75 using 1.5 M sodium hydroxide. The solution was diluted to 250 mL using deionized water. The running buffer was filtered and degassed before use.

Na$_2$HPO$_4$ (50 mM) with a pH of 7.7 was used as the sample dilution buffer. This was prepared by adding 1.7745 g of Na$_2$HPO$_4$ into 200 mL of deionized water and adjusting the pH with concentrated phosphoric acid to 7.7. The solution was then diluted to the volume of 250 mL using deionized water. This buffer was used to dissolve pteridine standards and dilute urine samples.

Preparation of the Pteridine Standards. Since pteridines tend to dissolve under alkaline conditions, 2 mg of each of the eight different pteridines was added into different bottles and dissolved with 9.7 mL of sample dilution buffer and 0.3 mL of 1.0 M sodium hydroxide to prepare sample stock solutions. The concentration of each of the stock solutions was calculated to be 0.2 mg/mL; they were diluted to required concentrations using the sample dilute buffer. Since the pteridines can be easily degraded under normal light, the samples were prepared under yellow light and all the bottles were covered by aluminum foil.

Collection and Treatment of Urine Samples. The urine samples of healthy persons were collected from student volunteers at Truman State University (Kirksville, Mo.). Cancer patient samples were obtained from the Cancer Treatment Center of Northeast Missouri Regional Medical Center (Kirksville, Mo.). Although early morning urine samples were collected, the concentration ratio of pteridine to creatinine in the urine samples was found to keep constant throughout the day. The samples were delivered in a dark box with ice and were wrapped with aluminum foil immediately upon receiving them to avoid photolysis. Fresh urine was treated following the procedure used by Trehan,[11] with a few modifications. To oxidize the pteridines from its reduced form in alkaline condition, 10 $\mu$L of 2 M sodium hydroxide and 10 $\mu$L of 2% $I_2$-4% KI solution were added into 100 $\mu$L of urine. The mixture was incubated in a dark box for 30 min at 4° C., and then the urine was centrifuged at 5000 rpm using the Eppendorf Centrifuge 5403 system for 20 min at 4° C. The supernatant was decanted to another vial and was diluted 10 times with sample dilution buffer for analysis. Freezing of the sample was not recommended because the level of some pteridines may change after freezing and thawing.

HPCE System. A home-built CE-LIF system was used in this study. The high-voltage power supply was purchased from Spellman (Plainview, N.Y.; model CZE 1000R). A 50 $\mu$m i.d.×60 cm fused-silica capillary (Polymicro Techniques, Phoenix, Ariz.) was used for the separation.

The capillary was pretreated with 1.0 M sodium hydroxide for 30 min followed by water rinsing to clean the capillary. The polymer coating was burned off 25 cm from the cathodic end of the capillary to form the detection window. The anodic high-voltage end of the capillary was isolated in a plexiglass box for safety while the cathodic end was held at ground potential.

A helium-cadmium laser (Liconix, Santa Clara, Calif.; model 4240NB) operating at 325 nm was used for excitation. A band-pass filter (250–400 nm, Ealing, Holliston, Mass.; model UG-11) was employed to reject stray and scattered radiation from the laser head. The laser was focused onto the capillary with a 1-cm focal length lens, and the fluorescence was collected with a 10×microscope objective at a 90° angle to the incident light. The fluorescent image was focused onto a silicon photodiode combined with a built-in amplifier (Hamamatsu, Bridgewater, N.J.; model HC220-01). Another band-pass filter (400–539 nm, Ealing; model 35-532) was used to isolate the fluorescence from pteridines. The voltage from the photodiode was monitored with an autoranging microvolt DMM (Keithley, Cleveland, Ohio; model 197A), and the data were collected and processed using the Isco ChemResearch 150 software.

HPCE Separation. Electrokinetic injection was performed by introducing standards and samples by applying a 20-kV voltage (positive at inlet end) for 10 s. Electrophoresis was carried out at 20 kV for 10 min. the capillary was regenerated by flushing with 0.2 M sodium hydroxide for 1 min after each run followed by a 2-min water rinse and another 2-min buffer rinse. The purpose of this procedure is to ascertain the best separation and reproducibility. Pteridines in urine were identified by the standard addition method. To control for the physiological concentration, the amount of pteridines were reported as a ratio of pteridine and creatinine ($\mu$g of pteridine/mg of creatinine). Creatinine in urine was determined by the HPLC method described by Shi, H. et al., *Anal. Chim. Acta* 1995, 312, 79–83.

RESULTS

Figure 2:
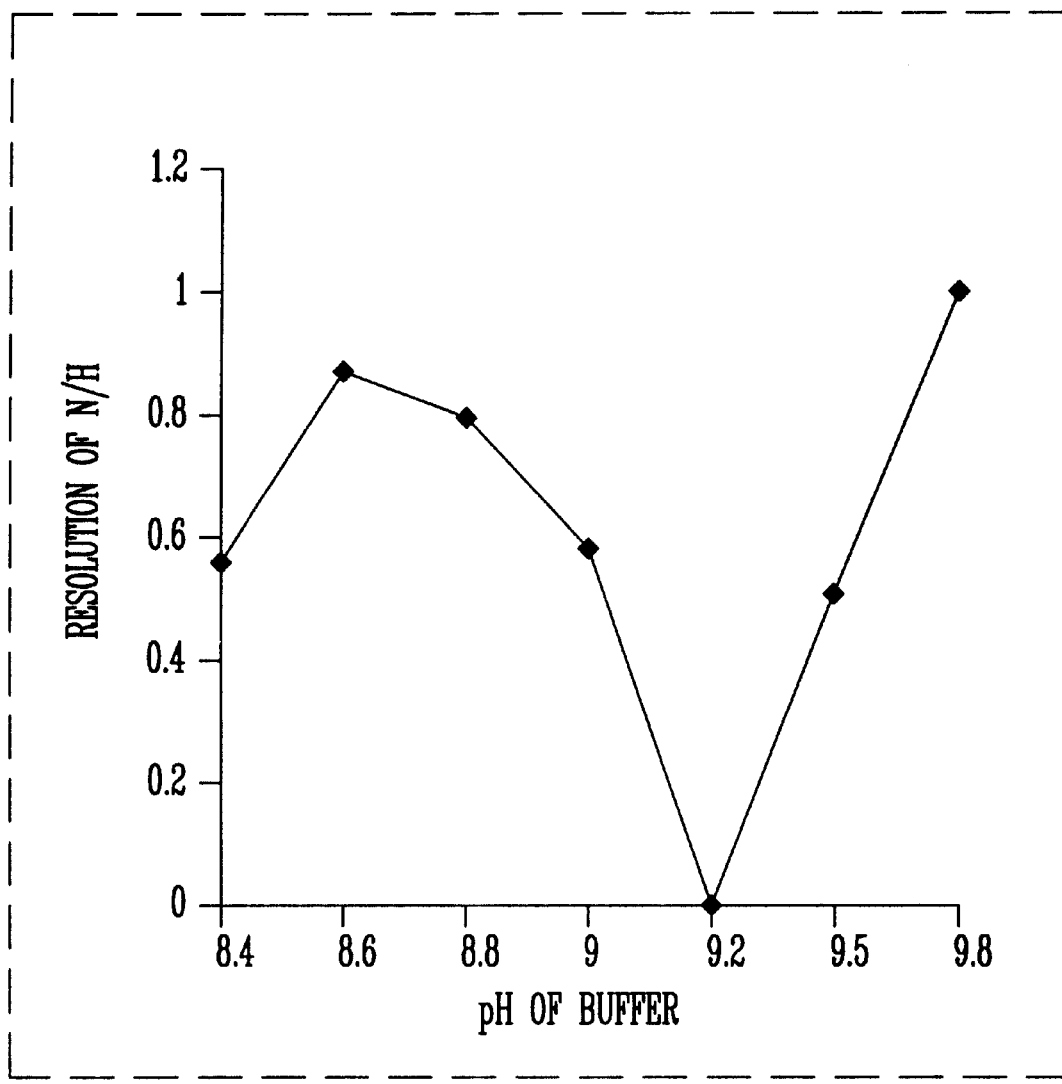
FIG. 2 displays the resolution of D-(+)-neopterin and 6-(hydroxymethyl)pterin under different pH's as described in Example 1.

From FIG. 1, it can be readily appreciated that all eight pteridines are well separated within 10 minutes. It was found that the separation of the pteridines was very pH sensitive. Good separation can be obtained only within a narrow range of pH. The resolution of some pteridines decreased when the buffer pH deviated from the optimized point. At pH under 8.0, there was no separation of 6-biopterin and D-(+)-neopterin, which are among the most important pteridines excreted in urine. The separations of neopterin and 6-(hydroxymethyl)pterin are especially sensitive to pH fluctuation due to similar molecular structure. FIG. 2 shows the resolution of these two compounds under different pH's. the resolution was calculated using a well-accepted equation used in chromatography. Good separation of all the standards can be achieved at pH 8.6–8.8. No separation of these two compounds was achieved at pH 9.2, and it was also found that the peak order reversed when the pH deviated from this point. Although the resolution of these compounds tends to increase at higher pH (>9.8), the separation of 6-biopterin and 6,7-dimethylpterine got worse with an increase of pH (data not shown).

The limits of detection (LOD) changed with the change of sample matrix. Because electrokinetic injection was employed in the study, the ionic strength of the sample matrix influenced the injection of the samples. Samples prepared in deionized water, in the running buffer, and in the phosphate buffer were investigated, respectively. It was found that the sample in deionized water gave the lowest peak area (data not shown). This phenomenon did not match what Cha et al. observed because pressure injection was used in their study. Cha, K. W. et al. *Pteridines* 1993, 4, 210–213. Since the conductivity of this sample matrix was too low and there were only a few sample molecules being injected onto the capillary, on-column stacking could not compensate for the inefficiency of the electrokinetic injection of the water-based sample. Table 1 lists the detection limits of the eight kinds of pteridines in running buffer and phosphate buffer matrixes:

TABLE 1

Detection Limits (g/mL) of Pteridines in Different Sample Matrixes

| Pteridines | Running Buffer | Phosphate Buffer |
| --- | --- | --- |
| 6,7-dimethylpterine | $8.9 \times 10^{-11}$ | $4.0 \times 10^{-11}$ |
| 6-biopterin | $2.5 \times 10^{-10}$ | $1.3 \times 10^{-10}$ |
| D-(+)-neopterin | $2.7 \times 10^{-10}$ | $1.3 \times 10^{-10}$ |
| 6-(hydroxymethyl)pterin | $2.0 \times 10^{-10}$ | $9.8 \times 10^{-11}$ |
| pterine | $1.8 \times 10^{-10}$ | $8.0 \times 10^{-11}$ |
| isoxanthopterin | $2.3 \times 10^{-10}$ | $1.3 \times 10^{-10}$ |
| xanthopterin | $2.6 \times 10^{-10}$ | $1.1 \times 10^{-10}$ |
| pterin-6-carboxylic acid | $4.8 \times 10^{-10}$ | $2.0 \times 10^{-10}$ |

As shown by Table 1, the sample in phosphate buffer resulted in the lowest detection limits. The conductivity of the buffers was measured and it was found that the conductivity of the phosphate buffer was higher than that of the running buffer. According to the observation of Huang et al., more samples will be introduced onto the capillary if the conductivity of the sample matrix is lower. Huang, X. et al., *Anal. Chem.* 1988, 60, 375–377. The inventor's result was not in accordance with their observation. It is believed that the reason leading to this phenomenon may be the complex formation between boric acid and the pteridines which influences the efficiency of electrokinetic injection. Simple pteridine molecules will be injected onto the capillary with high efficiency in the phosphate buffer and the pteridine-borate complex will be injected onto the capillary with much lower efficiency in the Tris-boric acid buffer. This kind of discrimination results in a lower level of detection (LOD) for the pteridines in the phosphate buffer. From these experiments, it was also determined that the sample matrix does not have significant influence on resolution.

Figure 3:
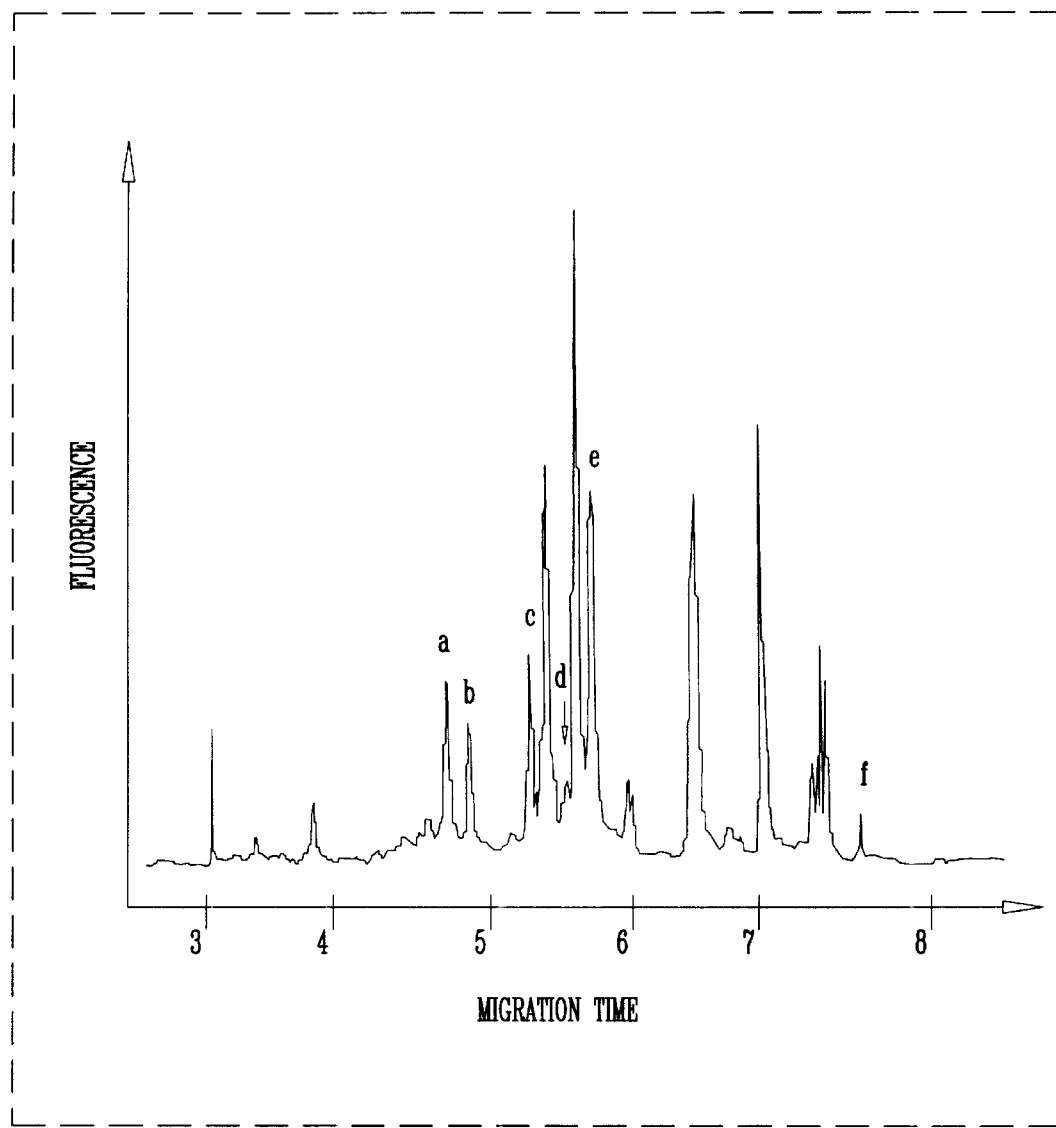
FIG. 3 is an electropherogram of the urine sample as described in Example 1. Conditions were the same as in FIG. 2. Peak identification: a, 6-biopterin; b, D-(+)-neopterin; c, pterine; d, isoxanthopterin; e, xanthopterin; f, pterin-6-carboxylic acid.

The levels of the pteridines were measured in 10 randomly selected healthy persons and 9 cancer patients with different tumors. There was no diet restriction on those subjects and no gender and age restriction also. All the tumor patients carried newly diagnosed tumors and they undertook no chemotherapy treatment because it Was found that chemotherapy greatly influenced the separation and identification of pteridines. Quantitation was accomplished by means of calibration curves with linear coefficients above 0.997 (data not shown). Six pteridines, 6-biopterin, D-(+)-neopterin, pterine, isoxanthopterin, xanthopterin, and pterin-6-carboxylic acid, were detected and identified in urine excreted by both normal subjects and cancer patients. FIG. 3 shows the typical electropherogram of a normal urine sample, in which peaks were identified by adding standards into the sample. It was found that there was no significant difference among those who were in the same group and with different genders and ages and that there was only a quantitation difference between normal persons and patients.

Figure 4:
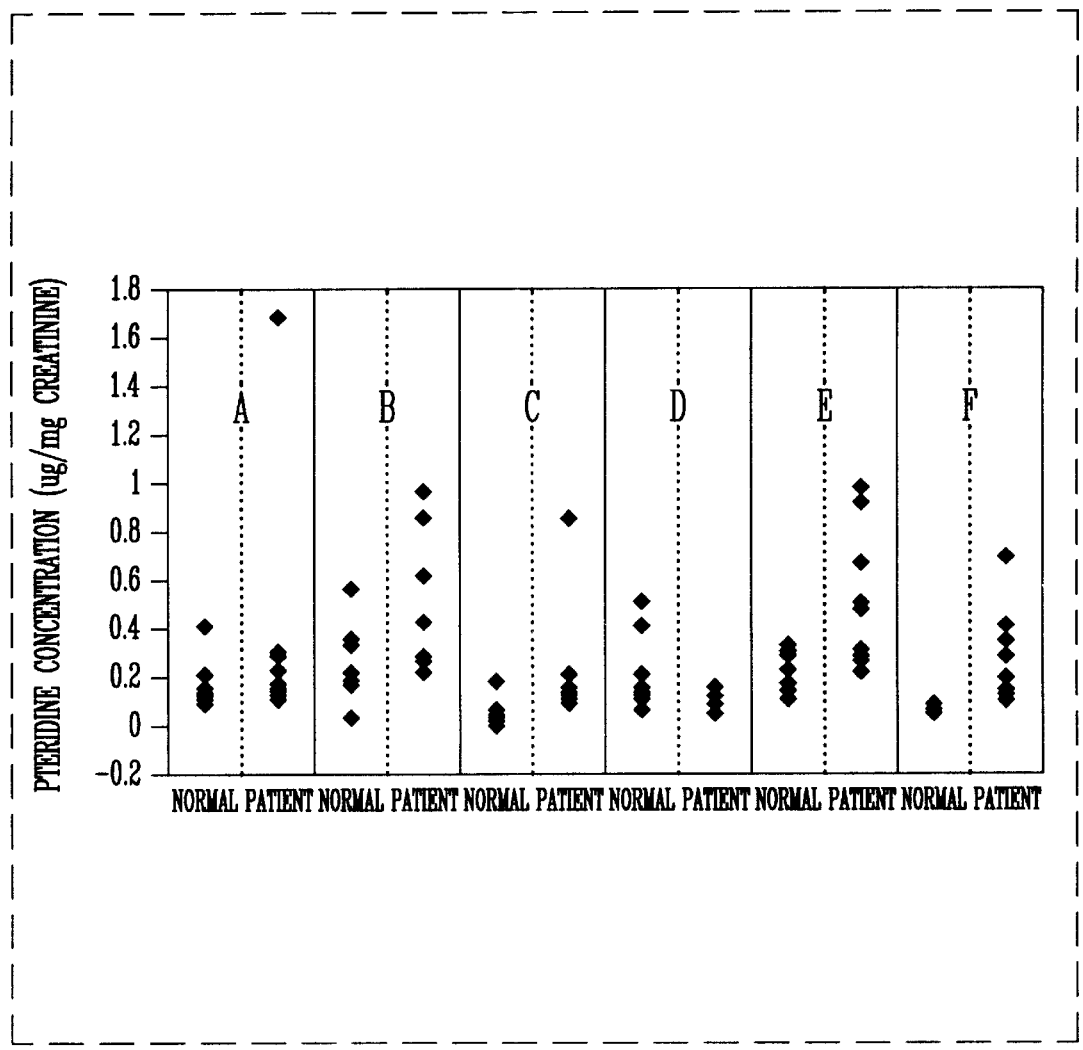
FIG. 4 is a scattergram of pteridine levels ($\mu$g/mg of creatinine) in normal persons and in cancer patients as described in Example 1. A, 6-biopterin; B, D-(+)-neopterin; C, pterine; D, isoxanthopterin; E, xanthopterin; F, pterin-6-carboxylic acid.

The levels of the six pteridines of the normal and cancer subjects and the results of T tests are listed in Table 2, and FIG. 4 shows the scattergram of pteridine levels in both normal and cancer subjects.

TABLE 2

Average Pteridine Levels Excreted in Urine by Normal Subjects and Cancer Patients

| Pteridine | Healthy Persons ($\mu$g/mg of creatinine) | Cancer Patients ($\mu$g/mg of creatinine) | Significant Levels |
| --- | --- | --- | --- |
| 6-biopterin | 0.19 | 0.17 | not significant |
| D-(+)-neopterin | 0.26 | 0.47 | $p < 0.05$ |
| pterine | 0.05 | 0.14 | $p < 0.01$ |
| isoxanthopterin | 0.21 | 0.04 | $p < 0.01$ |
| xanthopterin | 0.18 | 0.44 | $P < 0.05$ |
| pterin-6-carboxylic acid | 0.02 | 0.31 | $p < 0.001$ |

It was found that the levels of D-(+)-neopterin, pterine, xanthopterin, and pterin-6-carboxylic acid were significantly elevated in the cancer patients, while the level of isoxanthopterin decreased significantly. There was no significant change of biopterin level in cancer subjects. Since some investigators employed neopterin/biopterin ratio as a criterion (Stea, B. et al., Clin. Chim. Acta 1981, 113, 231–242), this ratio was also observed. There was an elevation to this ratio: the mean level of neopterin/biopterin for normal persons was 1.38, and the mean level for cancer patients was 2.19; that was 1.59 times that of normal persons. This observation correlates with what Stea et al. observed in which the neopterin/biopterin level for cancer patients was 1.6 times that of normal subjects.

Contrary to previous observations, 6-(hydroxymethyl)-pterin was not detected in the study. The previous studies either employed HPLC for qualitation and quantitation or employed thin-layer chromatography for qualitation and spectrophotofluorometer for quantitation. These methods are time-consuming and labor-intensive with unsatisfactory separation. So, some other materials with the same elution time may be identified as one material and may result in misleading quantitation. Another conflict with previous studies was that a significant enhancement of pterin-6-carboxylic acid excreted in urine of cancer patients was found in the study as compared to little increase observed in others. (See e.g. Stea et al.).

As shown, the CE-LIF method of the present invention is a fast, simple, and more reliable method of detecting pteridines in clinical and biochemical samples. Due to the significant enhancement of certain types of pteridines excreted in urine by patients carrying malignant disease, the method is useful in screening patients for cancer and monitoring the severity of patients already diagnosed with cancer. It is therefore submitted that the invention accomplishes at least all of its stated objectives.

It should be appreciated that minor modifications of the compositions and the ranges expressed herein may be made and still come within the scope and spirit of the present invention.

Having described the invention with reference to particular compositions, theories of effectiveness, and the like, it will be apparent to those of skill in the art that it is not intended that the invention be limited by such illustrative embodiments or mechanisms, and that modifications can be made without departing from the scope or spirit of the invention, as defined by the appended claims. It is intended that all such obvious modifications and variations be included within the scope of the present invention as defined in the appended claims. The claims are meant to cover the claimed components and steps in any sequence which is effective to meet the objectives there intended, unless the context specifically indicates to the contrary.

What is claimed is:

1. A method for measuring the concentration of pteridines in a biological sample comprising:
    collecting a biological sample;
    separating said sample through a capillary by electrophoresis through a capillary to form a separated sample, said electrophoresis including a running buffer that includes up to about 2 mM EDTA;
    irradiating said sample with radiation;
    detecting a fluorescence emission of the sample from the irradiation thereof; and
    analyzing the emission to determine the presence of pteridines in the sample.

2. A method according to claim 1 whereby the pH of the running buffer is within the range of about 8.4 to about 9.0.

3. A method according to claim 2 wherein the pH of the running buffer is within the range of about 8.6 to about 8.8.

4. A method according to claim 1 whereby the volume of the sample used in the separation step is from about 10 to about 100 $\mu$l.

5. A method according to claim 1 further including a sample matrix having a high ionic strength.

6. A method according to claim 5 whereby the sample matrix is phosphate buffer.

7. A method according to claim 1 whereby the sample is irradiated using radiation having a wavelength of between about 270 nm to about 345 nm.

8. A method according to claim 7 whereby the sample is irradiated using radiation having a wavelength of about 325 nm.

9. A method according to claim 1 enabling detection of pteridine compounds at detection limits of less than about $1 \times 10^{-10}$ M.

10. A method according to claim 1 wherein the biological sample is a urine sample.

11. A method according to claim 1 wherein the running buffer further includes up to about 2 mM of EDTA.

12. A method of monitoring and screening for cancer in a mammal comprising:
collecting a biological sample;
separating said sample through a capillary by electrophoresis through a capillary to form a separated sample, said electrophoresis including a running buffer;
irradiating said sample with radiation;
detecting a fluorescence emission of the sample from the irradiation thereof;
analyzing the emission to determine the concentration of pteridines in the sample; and
comparing the concentrations of pteridines in the sample with the concentration of pteridines in a biological sample from a healthy mammal of the same species to determine whether the concentrations of pteridines are significantly elevated or decreased.

13. A method according to claim 12 whereby the pH of the running buffer is within the range of about 8.4 to about 9.0.

14. A method according to claim 12 whereby the pteridines detected are selected from the group consisting of 6,7-dimethylpterin, 6-biopterin, D-(+)-neopterin, 6-(hydroxymethyl)pterine, pterine, isoxanthopterin, xanthopterin, and pterin-6-carboxylic acid.

15. A method according to claim 12 the levels of D(+)-neopterin, pterine, xanthopterin, and pterin-6-carboxylic acid are significantly elevated in a mammal with cancer compared to a healthy mammal of the same species.

16. A method according to claim 12 whereby the level of isoxanthopterin is significantly decreased in a mammal with cancer compared to a healthy mammal of the same species.

* * * * *